United States Patent [19]

Theeuwes

[11] Patent Number: 4,540,403
[45] Date of Patent: Sep. 10, 1985

[54] PARENTERAL DISPENSING SYSTEM WITH PROGRAMMABLE DRUG ADMINISTRATION

[75] Inventor: Felix Theeuwes, Los Altos, Calif.

[73] Assignee: Alza Corporation, Palo Alto, Calif.

[21] Appl. No.: 626,908

[22] Filed: Jul. 2, 1984

[51] Int. Cl.³ .............................................. A61M 5/14
[52] U.S. Cl. ..................................... 604/85; 604/251; 204/299 R
[58] Field of Search ....................... 604/83, 80, 81, 84, 604/85, 890, 892, 251; 204/299, 302

[56] References Cited

U.S. PATENT DOCUMENTS

| | | | |
|---|---|---|---|
| 3,976,068 | 8/1976 | Lundquist | 604/56 |
| 4,149,957 | 4/1979 | Gibson et al. | 204/299 X |
| 4,233,973 | 11/1980 | Shukla | 604/84 |
| 4,439,183 | 3/1984 | Theeuwes | 604/85 |
| 4,484,909 | 11/1984 | Theeuwes et al. | 604/85 X |

Primary Examiner—Stephen C. Pellegrino
Attorney, Agent, or Firm—Paul L. Sabatine; Edward L. Mandell; Steven F. Stone

[57] ABSTRACT

A parenteral delivery system is disclosed for administering a beneficial agent to an agent-receiving recipient. The parenteral system comprises an electrotransport apparatus that admits an agent at an electrically controlled rate into medical fluid that flows through the parenteral system over delivery time.

30 Claims, 5 Drawing Figures

PARENTERAL DISPENSING SYSTEM WITH PROGRAMMABLE DRUG ADMINISTRATION

FIELD OF THE DISCLOSURE

The subject matter disclosed and claimed herein pertains to a parenteral delivery system. The parenteral delivery system comprises a reservoir containing a parenterally acceptable administrable fluid, a drip chamber, and an electrotransport apparatus containing a drug. In operation, the electrotransport apparatus delivers drug at a controlled rate into the parenteral fluid that flows through the parenteral system.

BACKGROUND OF THE DISCLOSURE

The parenteral administration, including intravenous administration of beneficial fluids is commonly used in clinical practice. Presently, beneficial drugs also are administered by using a parenteral delivery system. The parenteral system used for administering the beneficial drug generally consists of a reservoir that contains a premixed formulation consisting essentially of the beneficial drug and a parenterally administrable fluid. The premixed formulation is administered by gravitational flow by suspending the reservoir above the patient.

While this form of parenteral administration is widely used and often leads to successful therapy, there is still a great deal of clinical dissatisfaction with the chemotherapy of parenteral delivery systems. For example, the parenteral system frequently overdoses, or it underdoses outside of the therapeutically effective range, the parenteral system does not permit exact dosing of the medicament, and the parenteral delivery system is not programmable for delivering a drug according to the needs of a patient.

OBJECTS OF THE DISCLOSURE

Accordingly, in view of the above presentation, it is an immediate object of the present invention to provide a parenteral delivery system that overcomes the short comings associated with the prior art.

Another object of the invention is to provide a parenteral delivery system that permits exact dosing of an effective medicament according to the needs of a patient.

Another object of the invention is to provide a parenteral delivery system useful for chemotherapy obtained by controlled medication within a predetermined therapeutically effective range.

Another object of the invention is to provide a parenteral delivery system that is useful for the programmed delivery of a chemotherapeutic agent.

Another object of the invention is to provide a parenteral delivery system that comprises means for programming chemotherapy delivery including adjusting the delivery to on, off, continuous, or a variable rate consisting of low to high amounts of agent delivery over time.

Another object of the invention is to provide a parenteral system for delivering a drug intravenously by electrotransport for controlled medical treatment.

DETAILED DESCRIPTION OF THE DRAWINGS

Figure 1:
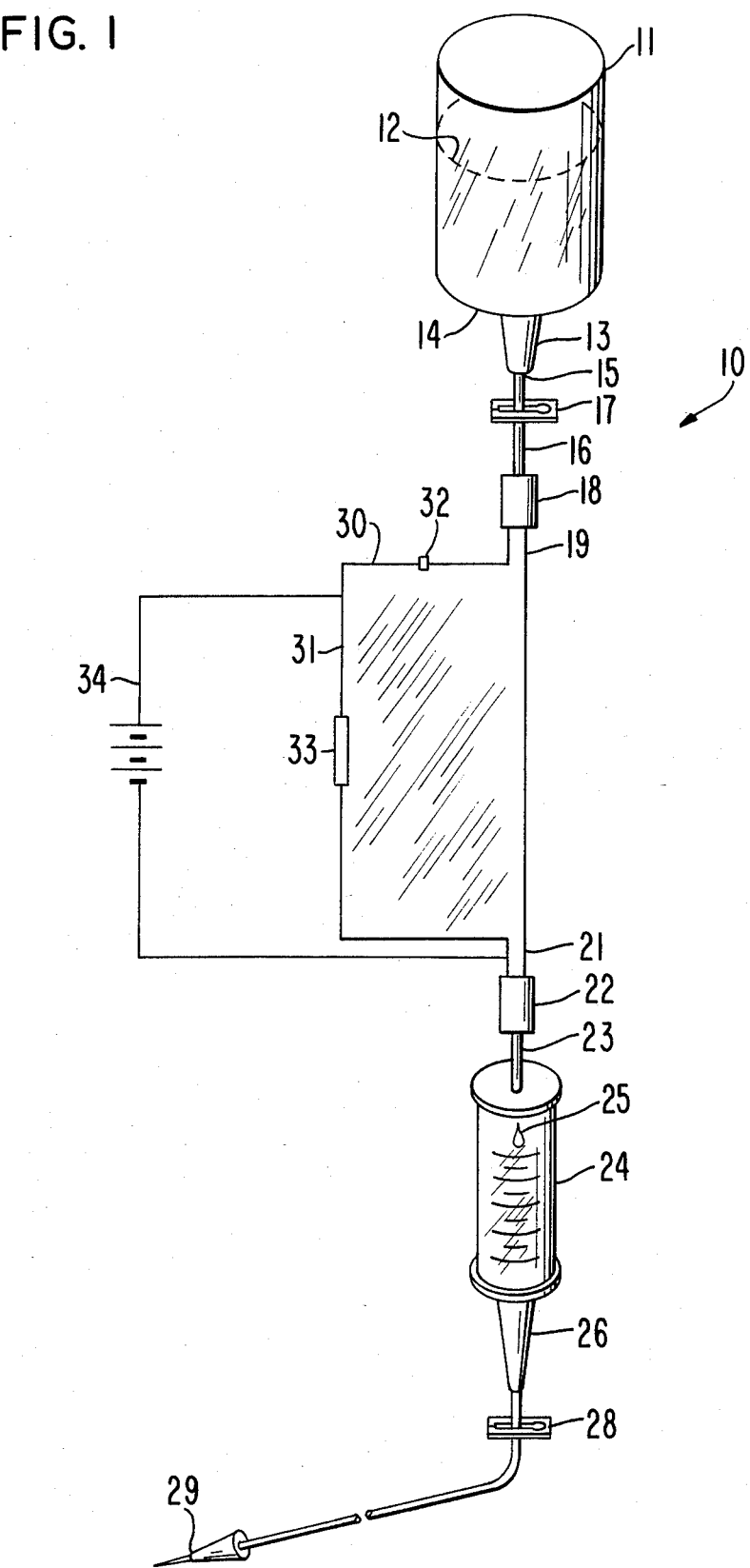
FIG. 1 is a view of a parenteral delivery system provided by the invention comprising a primary fluid path having an electrotransport drug delivery mechanism releasably connected to the primary path.

FIG. 1 represents a parenteral delivery system 10 provided by the invention. Parenteral delivery system 10, as used herein, includes intravenous delivery. Parenteral delivery system 10 comprises a reservoir 11 of a medically acceptable fluid 12 suitable for parenteral including intravenous administration. Reservoir 11 is made of plastic, preferably of clear, transparent, non-toxic plastic. Reservoir 11 also can be made as a glass container. In the embodiment illustrated, reservoir 11 is shaped like a glass container. Reservoir 11 is connected to the rest of parenteral delivery system 10 through fluid conveying member 13 suitably formed with the bottom 14 of reservoir container 11. Fluid conveying member 13 is hollow and it conveys fluid 12 from reservoir 11 to the rest of delivery system 10. The other end 15 of fluid conveying member 13 is connected to a section of a medical grade tubing 16. Tube 16 passes through a fluid regulating clamp 17 used for adjusting the rate of fluid 12 flow through parenteral delivery system 10. The other end of tube 16 is connected to a couple 18 that receives the fluid inlet port 19 of electrostransport apparatus 30. The fluid outlet port 21 is suitably connected to a couple 22. A second section of medical grade tube 23 conveys fluid 12 from couple 22 to a drip chamber 24. Drip chamber 24 is preferably transparent and it is made from glass or from a clear plastic. Drip chamber 24 is used to trap air, and it is used in cooperation with regulator clamp 17 for adjusting the rate of flow of medical fluid dropwise 25 through system 10. Drip chamber 24 has an outlet 26 suitably connected to a section of medical grade tubing 27 that passes through regulator clamp 28 and terminates by connecting to a skin piercing delivery member 29 for administering fluid 12 to a patient.

Electrotransport apparatus 30 is seen in closed section in FIG. 1. Electrotransport apparatus 30 comprises a housing 31 that surrounds an internal space not seen in FIG. 1. Housing 31 comprises a wall or walls formed of a material substantially impermeable to the passage of drug and substantially impermeable to the passage of fluid. Electrotransport apparatus 30 is provided with a vent 32 for letting gas escape from electro transport apparatus 30, and it is provided with a filling port 33. Port 33 is a piercable access port formed of a selfclosing material and it is used for admitting a drug or a fluid into electrotransport apparatus 30. A source of electrical energy 34 is provided for supplying electricity to a pair of electrodes contained in electrotransport apparatus 30, not seen in FIG. 1. A detailed description of electrotransport apparatus 30 is presented latter in the specification.

Figure 2:
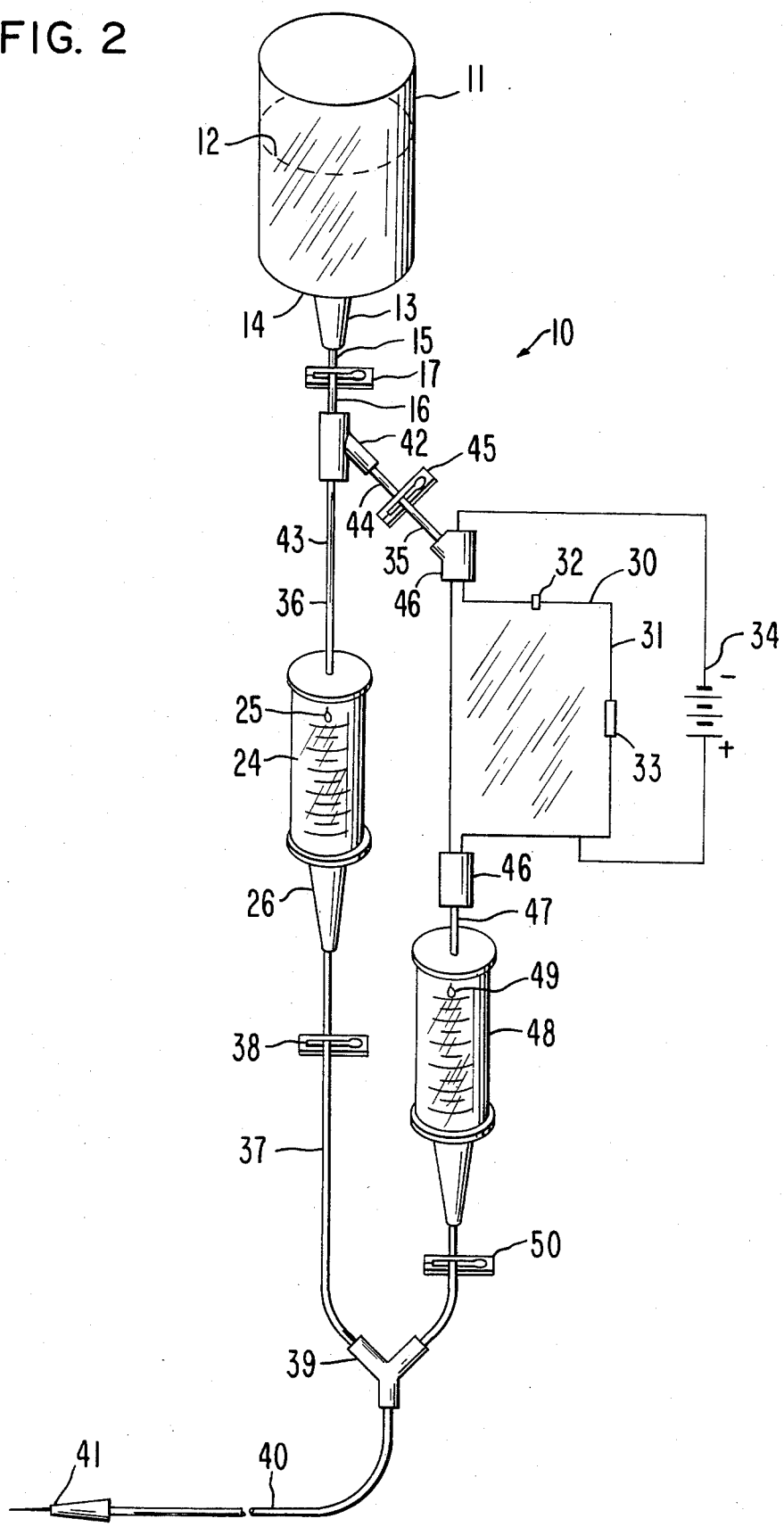
FIG. 2 is a view of a parenteral delivery system provided by the invention comprising a primary path and a by-pass path, which by-pass path consists essentially of an electrotransport apparatus releasably connected to the by-pass path for delivering a drug into the by-pass path.

FIG. 2 depicts another embodiment of the parenteral delivery system provided by the invention. FIG. 2 depicts a parenteral delivery system 10 similar to the system depicted in FIG. 1; however, in FIG. 2 parenteral delivery system 10 comprises a secondary fluid path 35 that has electrotransport apparatus 30 suitably releasably connected thereto. The presence of secondary fluid path 35 allows the primary path 36 to administer medical fluid 12 free of drug added by using electrotransport apparatus 30. Thus, fluid 12 can flow from reservoir 11 through primary path 36, through drip chamber 24, and into tube 37. Tube 37 passes through a regulator clamp 38 and conveys fluid to Y couple means 39. Couple 39 is a means for joining fluid flow from primary path 36 and fluid flow from secondary path 35 into common path 40. Common path tube 40 is connected to a skin-piercing means 41 for administering fluid 12 or fluid 12 containing drug to a patient. Secondary path 35 is connected to primary path 36 through couple 42. Couple 42 has an inlet for receiving tube 16, for receiving tube 43 that conveys fluid 12 to drip chamber 24, and for receiving tube 44. Tube 44 passes through flow regulator 45 and into couple 46. Couple 46 additionally receives one end of electrotransport apparatus 30. The downstream end of electrotransport apparatus 30 is connected to couple 46. A section of tube 47 conveys a drug solution from electrotransport apparatus 30 into drip chamber 48. The rate of flow of drug solution through formulation chamber 48 is regulated dropwise 49 by regulator 50. A section of tube 51 passes through regulator 50 into couple 39 for flow into tube 40.

Figure 3:
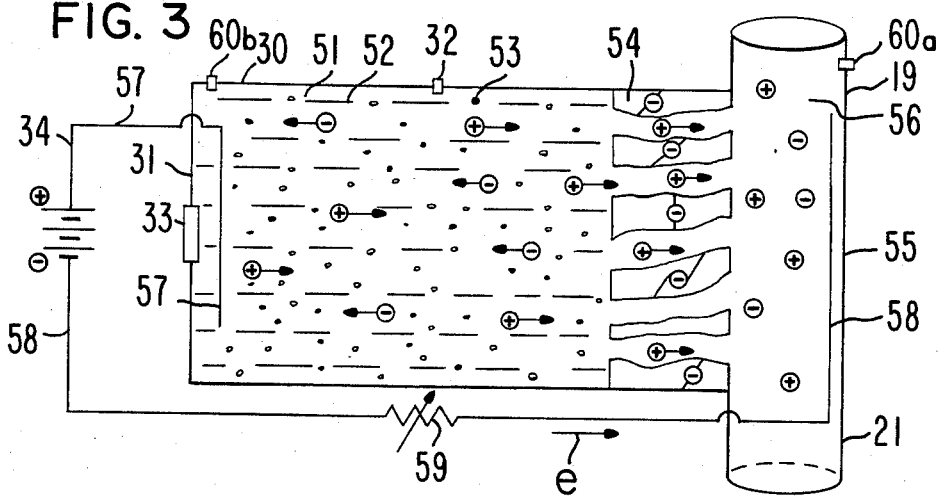
FIG. 3 is an open view that schematically illustrates an electrotransport apparatus comprising a cation exchange membrane useful for delivering a drug into a parenteral fluid path.

In FIG. 3 electrotransport apparatus 30, for use in FIGS. 1 and 3, is seen in opened section. In FIG. 3, electrotransport apparatus 30 is enlarged for illustrating its components; however, electrotransport apparatus 30 is readily miniaturized, and it is thus capable of being used as a portable unit with parenteral delivery systems. Moreover, since electrotransport apparatus 30 is driven electrically and since it has no moving parts, it may be instantaneously turned on and off, and therefore it may be programmed to dispense drug in an infinite variety of time-delivery patterns. The dispensing rate may be varied by varying the electrical input, and the electrotransport apparatus, if desired, is capable of being controlled remotely.

Further in FIG. 3, electrotransport apparatus 30 comprises wall 31 that surrounds internal space 51. Internal space 51 contains fluid 52 and drug 53. Wall 31 is made of a material substantially impermeable to the passage of fluid 52 and drug 53. Electrotransport apparatus 30 additionally comprises an inner wall 54 formed of (a) an ion exchange material, or (b) a porous material. In FIG. 3, inner wall 54 presently is illustrated formed of an ion exchange material such as a cation exchange membrane. A typical cation exchange membrane is formed from a sulfonated cross-linked polystyrene such as poly(styrene trimethyl ammonium sulphate) crossed linked with divinyl benzene. In FIG. 3, when inner wall 54 is formed of a porous material, it can be formed from quartz, glass or ceramic. Generally, the porous material will have a pore size of 0.002 $\mu$ to about 10 $\mu$, and a porosity of about 10 to 70 percent. Inner wall 54 and distant wall 55 of electrotransport apparatus 30 form a passageway 56, which passageway 56 is suitable for (1) connecting apparatus 30 to the primary, or the secondary path of parenteral delivery system 10, (2) for receiving fluid 12 from reservoir 11, and (3) for receiving drug 53 moving under the influence of an electrical field in internal space 51. Apparatus 30 comprises a pair of electrodes comprising cathode electrode 58 placed inside internal space 51 and a distant anode electrode 57 placed inside passageway 56. Anode 57 is connected to the positive pole of an electrical power source 34, and cathode 58 is connected to the negative pole of the same electrical power source 34. Typically a battery can be used as a d.c. power source. A variable rheostat 59 is provided on the cathode electron path for regulating the flow of electrons. Inner walls 54, optionally formed of an ion exchange material, or optionally formed of a porous material, is interposed between the electrodes.

Anode electrode 57 and cathode electrode 58 can be made from conventional materials. Typical materials used for making electrodes include silver, platinum, copper and the like. In a presently preferred embodiment, the electrodes are selected which do not produce appreciable amounts of unwanted gas produced through electrolysis and which do not polarize. The electrodes suitable for this purpose include silver-silver chloride electrodes, and the like. Electrotransport apparatus 30 is provided with optional vents 60$a$ and 60$b$ that can be connected to a charcoal gas scavenger trap, not shown, for collecting any gas that may be produced during operation of the electrotransport drug delivery apparatus 30.

Electrotransport drug delivery apparatus 30 delivers drug 53 by electrodialysis or by electroosmosis. Electrotransport apparatus 30 operates to deliver drug by electrodialysis when internal wall 54 is formed of an ion exchange material such as a cation exchange membrane, and drug 53 exhibits the ability to ionize, such as salbutamol hydrochloride. The drug is delivered in this operation when a voltage difference is applied across anode 57 and cathode 58 through cation exchange membrane 54 interposed between the electrodes and adjacent to passageway 56. When the voltage difference is applied, fluid and drug will flow through the cation exchange membrane in the direction indicated by the arrows attached to the positive charges. The drug will be transported through cation exchange membrane 54 into medical fluid 12 flowing through passageway 56 for administration to a patient. Electro-transport apparatus 30 operates to deliver drug 53, when wall 54 is formed of a porous material and when a drug 53 such as hydrocortisone is essentially neutral, in an electrical field by electroosmosis. In electroosmosis, wall 54 acts as a stationary solid porous body through which a fluid will pass. By applying a potential difference to the electrotransport apparatus, fluid will move through the porous body simultaneously transporting the neutral drug through the porous body into medical fluid 12 flowing through passageway 56.

Figure 4:
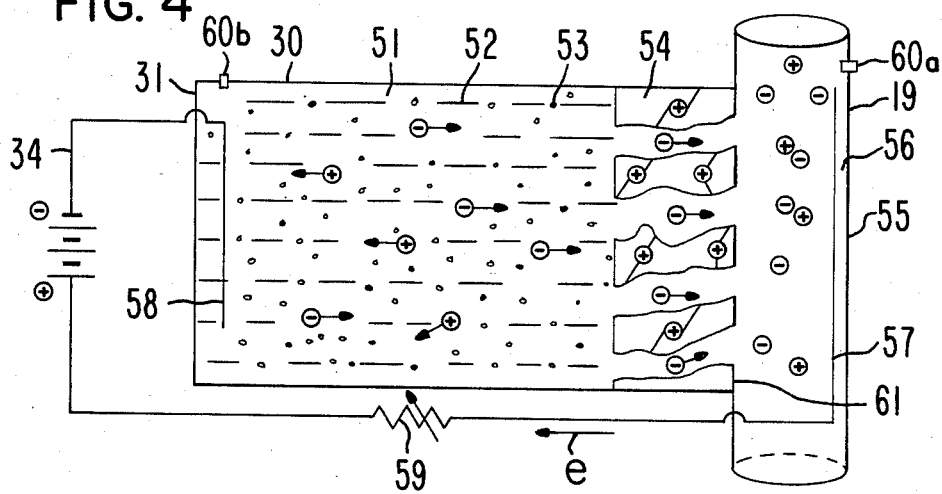
FIG. 4 is an opened view depicting schematically an electrotransport apparatus comprising an anion exchange membrane useful for delivering a drug into a parenteral delivery fluid path; and, FIG. 5 is an opened view that schematically illustrates another electrotransport arrangement for delivering a drug into a moving fluid parenteral including intravenous delivery path.

FIG. 4 illustrates another embodiment of electrotransport apparatus 30 that can be used with parenteral delivery system 10. The electrotransport apparatus of FIG. 4 can be used in the primary path and the secondary path of the parenteral system. In FIG. 4, electrotransport apparatus 30 is seen in opened section for illustrating its internal components. The electrotransport apparatus of FIG. 4 is similar to the electrotransport apparatus of FIG. 3. In FIG. 4, electrotransport apparatus 30 comprises wall 31 that surrounds internal space 51. Internal space 51 contains fluid 52 and drug 53. Internal space 51 additionally comprises an inner wall 54 formed of an anion exchange membrane. Exemplary anion exchange membranes are strong-base and weak-base materials, including anion exchange membranes where the active group is selected from quaternary ammonium, secondary amine, tertiary amines covalently bonded to an aromatic matrix and tertiary amines covalently bonded to an aliphatic matrix. The anion exchange materials include diethylaminoethylcellulose, triethylaminoethylcellulose, aceteolacellulose (the reaction product of epichlorohydrin, triethanolamine and cellulose), quaternary ammonium derivatives of styrene polymers, and the like. Anion exchange membranes are available as Amberlite ® IRA-400, Dowex ®-1, Ionac ® A-550, and the like. Inner wall 54, in another embodiment optionally can be a porous body formed for example, of quartz, glass or ceramic. Inner wall 54 has a surface 61 that forms with wall 55 a passageway 56 for the flow of drug and fluid through parenteral delivery system 10. Electrotransport apparatus 30 comprises two electrodes, cathode 58 placed inside space 51, and a distant anode 57 positioned inside passageway 56. Anode 57 and cathode 58 can be silver-silver chloride electrodes, and the like.

Electrotransport drug delivery apparatus 30 delivers drug 53 by establishing a voltage difference across cathode 58 and anode 57. In this operation, drug 53, such as sodium indomethacin useful as an anti-inflammatory, antipyretic, analgesic therapeutic, in fluid 52, such as an aqueous solution, in an electrical field will ionize and form a mobile drug with a negative charge that will move in the direction of the arrows attached to the circled negative signs. Drug 53 will be electrically transported through anion exchange membrane 54 into passageway 56, where it combines with hydrogen ion. In passageway 56, drug 53 then is transported in medical fluid 12 to a patient attached to parenteral delivery system 10.

Figure 5:
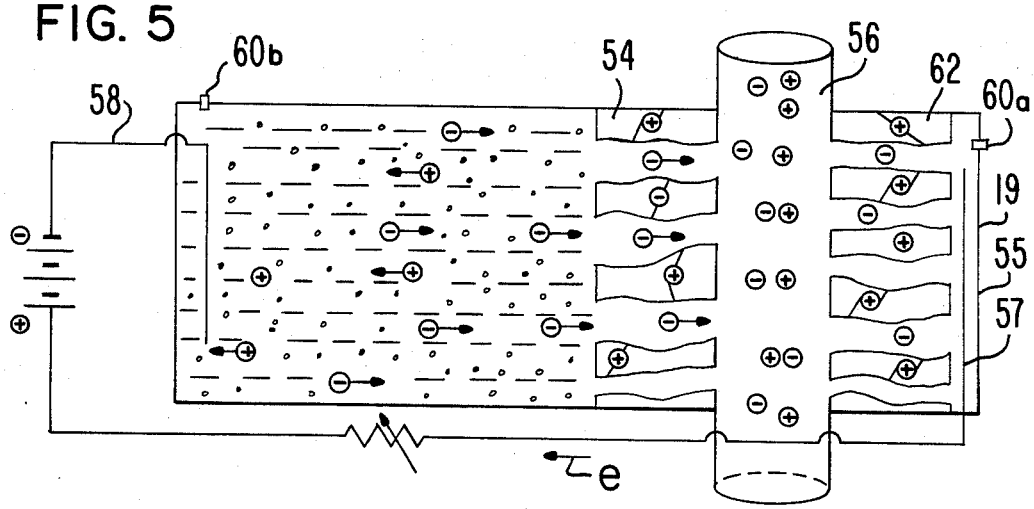

FIG. 5 illustrates another electrotransport apparatus 30 provided by the invention. Electrotransport apparatus 30 in FIG. 5 is seen in opened section and it is similar to electrotransport apparatus 30 as seen in FIG. 3 and in FIG. 4. In FIG. 5, electrotransport apparatus 30 comprises an additional ion exchange membrane 62, thereby providing an ion exchange membrane 62 and an ion exchange membrane 54 on each side of passageway 56. In FIG. 5, illustrated membranes 54 and 62 are depicted as anion exchange membrane. In another embodiment, membranes 54 and 62 can be cation exchange membranes accompanied by a reverse in the polarity of the electrodes as seen in FIG. 3. The addition of the second ion exchange membrane serves to lessen or avoid any possible reaction at the electrode when the electrode is positioned in fluid passageway 56 used as a drug delivery channel. By adding the second ion exchange membrane, electrolytes will diffuse through ion exchange membrane 62 towards electrode 57. In the environment of electrode 57, the unwanted electrolytes can be trapped or vented from the system thereby keeping them out of the drug delivery channel 56. In an additional embodiment membrane 54 can be porous and membrane 62 can be an ion exchange membrane. The electrotransport controlled drug delivery apparatus of FIG. 5 operates as described previously for electrotransport apparatus of FIGS. 3 and 4.

Medical fluid 12 in reservoir 11 is typically a sterile solution, such as a solution of dextrose, a solution of an electrolyte, or saline. Medical fluid 12 also is a pharmaceutical vehicle, or a pharmaceutically acceptable carrier for beneficial agent 53 that is to be administered to a recipient through delivery members 28 or 41. The initial volume of medical fluid 12 in container 11 will be a volume sufficient for performing a preselected therapeutic program. Container 11 can be a small volume container, or container 11 can be a large volume container. Container 11, as presently used herein, generally will have for a small volume container a capacity of about 100 cc to 350 cc, and a large volume container will have a capacity of 250 cc to 1000 cc. Containers of other capacities likewise can be used for the present purpose.

Fluid 52 initially housed, or subsequently injected into electrotransport apparatus 30 can be the same as medical fluid 12, or it can be different from medical fluid 12. Fluid 52 is used as a fluidic electrotransport vehicle or carrier, or it can be used as a fluidic medium through which a charged-bearing beneficial agent 53 moves towards passageway 56. In a presently preferred embodiment fluid 53 is compatible with fluid 12, and it is therapeutically acceptable to a host on parenteral therapy.

The beneficial agent 53 initially present in electrotransport apparatus 30 can be in any pharmaceutical state that lends itself to form a charge bearing agent. The charged bearing agent is formed under the influence of the flow of electrical current between the electrodes. The charged agent, after passing through the ion exchange membrane, or the porous membrane, combines with an oppositely charged ion formed by fluid 12 separating into ions, to yield a compound suitable for intravenous administration. Agent 53 housed in electrotransport apparatus 30 does not require any reconstituting, or admixture prior to use. The term beneficial agent as used herein includes drugs, which drugs are administrable to a recipient. The term recipient embraces warm-blooded animals, which latter expression includes humans. The pharmaceutically acceptable forms that can initially be charged into electrotransport apparatus 30 include solid forms such as crystalline, microcrystalline, particle, pellet, granule, powder, tablet, dry, spray-dried, lyophilized, forms that dissolve in the presence of fluid, forms solutions in the presence of fluids and the like. Electrotransport apparatus 30 generally contains an amount of beneficial agent 53 sufficient for executing a prescribed therapeutic program; that is, an amount of agent for the preprogrammed delivery of a therapeutically effective amount of agent to a recipient to produce a beneficial, therapeutic effect.

I claim:

1. A parenteral delivery system for administering a beneficial agent to a recipient, the delivery system comprising:
   I. a reservoir of a pharmaceutical fluid,
   II. an electrotransport apparatus for use with the parenteral system for admitting a beneficial agent into the pharmaceutical fluid, the electrotransport apparatus comprising:
      (a) a housing comprising a wall that surrounds an internal space;
      (b) means in the wall for (1) releasably connecting the electrotransport apparatus to the parenteral system, for (2) letting pharmaceutical fluid flow from the parenteral system with the electrotransport apparatus, and for (3) letting pharmaceutical fluid exit the electrotransport apparatus and reenter the parenteral system;
(c) a pair of electrodes in spaced relation disposed within the electrotransport apparatus;
(d) a cation exchange membrane interposed between the electrodes; and,
(e) a beneficial agent in the housing initially present between an electrode and the cation exchange membrane.

2. The parenteral delivery system for administering the beneficial agent according to claim 1, wherein the parenteral delivery system comprises a drug chamber.

3. The parenteral delivery system for administering the beneficial agent according to claim 1, wherein the beneficial agent is an intravenously administrable drug.

4. The parenteral delivery system for administering the beneficial agent according to claim 1, wherein the electrodes are connected to an electrical power source.

5. The parenteral delivery system for administering the beneficial agent according to claim 1, wherein the electrotransport apparatus comprises a fluid passageway in the housing extending from the fluid inlet in the wall to the fluid outlet in the wall.

6. The parenteral delivery system for administering the beneficial agent according to claim 5, wherein an electrode is disposed in the fluid passageway.

7. The parenteral delivery system for administering the beneficial agent according to claim 5, wherein the electrotransport apparatus comprises an additional cation exchange membrane and the fluid passageway is interposed between the two cation exchange membranes.

8. A parenteral delivery system for administering a beneficial agent to a recipient, the delivery system comprising:
I. a reservoir of a pharmaceutical fluid;
II. an electrotransport apparatus for use with the parenteral system for admitting a beneficial agent into the pharmaceutical fluid, the electrotransport apparatus comprising:
(a) a housing comprising a wall that surrounds an internal space;
(b) an inlet in the wall for letting fluid from the parenteral system enter the electrotransport apparatus;
(c) an outlet in the wall for letting fluid from the electrotransport apparatus exit the electrotransport apparatus and reenter the parenteral system;
(d) a pair of electrodes in spaced-apart relation positioned within the electrotransport apparatus;
(e) an anion exchange membrane interposed between the electrodes; and,
(f) a beneficial agent in the housing between an electrode and the anion exchange membrane.

9. The parenteral delivery system for administering the beneficial agent according to claim 8, wherein the parenteral delivery system comprises a drip chamber.

10. The parenteral delivery system for administering the beneficial agent according to claim 8, wherein the beneficial agent is an intravenously administrable drug.

11. The parenteral delivery system for administering the beneficial agent according to claim 8, wherein the electrodes are connected to an electrical power source.

12. The parenteral delivery system for administering the beneficial agent according to claim 8, wherein a fluid passageway is in the housing extending from the fluid inlet to the fluid outlet.

13. The parenteral delivery system for administering the beneficial agent according to claim 11, wherein an electrode is disposed in the fluid passageway.

14. The parenteral delivery system for administering the beneficial agent according to claim 11, wherein an additional anion exchange membrane is present in the electrotransport apparatus and the passageway is located between the two anion exchange membranes.

15. A parenteral delivery system for administering a beneficial agent to a recipient, the delivery system comprising:
I. a reservoir of a pharmaceutical fluid;
II. an electrotransport apparatus for use with the parenteral system for admitting a beneficial agent into the pharmaceutical fluid, the electrotransport apparatus comprising:
(a) a housing comprising a wall that surrounds an internal lumen;
(b) an inlet in the wall adapted for releasably connecting the electrotransport apparatus to the parenteral system;
(c) an outlet in the wall adapted for connecting the electrotransport apparatus to the parenteral system;
(d) a porous body in the housing, the porous body comprising a fluid entrance surface, a fluid exit surface, and being capable of carrying a surface charge;
(e) a pair of electrodes in the housing placed on each side of the porous body; and,
(f) a beneficial agent in the housing between an electrode and the fluid entrance surface of the porous body.

16. The parenteral delivery system for administering a beneficial agent according to claim 14, wherein the parenteral system comprises a drip chamber.

17. The parenteral delivery system for administering a beneficial agent according to claim 14, wherein the beneficial agent is an intravenously administrable drug.

18. The parenteral delivery system for administering a beneficial agent according to claim 14, wherein the electrodes are connected to an electrical power source.

19. The parenteral delivery system for administering the beneficial agent according to claim 14, wherein a fluid passageway is in the housing extending from the fluid inlet to the fluid outlet.

20. The parenteral delivery system for administering the beneficial agent according to claim 18, wherein an electrode is in the fluid passageway.

21. The parenteral delivery system for administering the beneficial agent according to claim 18, wherein an ion exchange membrane is in the housing and a passageway is positioned between the porous body and the ion exchange membrane.

22. A parenteral delivery system for administering a beneficial agent to a recipient, the delivery system comprising:
I. a reservoir of a pharmaceutical fluid;
II. an electrotransport apparatus for use with the parenteral system for admitting a beneficial agent into the pharmaceutical fluid, the electrotransport apparatus comprising:
(a) a housing comprising a wall that surrounds an internal lumen;
(b) an inlet in the wall for connecting the electrotransport apparatus to the parenteral system;
(c) an outlet in the wall for connecting the electrotransport apparatus to the parenteral system;

(d) a pair of spaced electrodes within the lumen;
(e) a porous body and an ion exchange member within the lumen and disposed between the electrodes, said body being capable of carrying a surface charge;
(f) a fluid passageway in the lumen, said passageway extending from the inlet to the outlet and interposed between the porous body and the ion exchange member; and,
(g) a beneficial agent in the lumen between the electrode, the porous body and the ion exchange member.

23. The parenteral delivery system for administering the beneficial agent according to claim 22 wherein the parenteral delivery system comprises a drip chamber.

24. The parenteral delivery system for administering the beneficial agent according to claim 22, wherein the electrodes are connected to an electrical power source.

25. The parenteral delivery system for administering the beneficial agent according to claim 22, wherein the internal lumen contains a fluid containing an electrolyte that is a intravenous carrier for the beneficial agent.

26. A parenteral delivery system for administering a beneficial agent to a recipient, wherein the parenteral system comprises:
I. a primary path, said primary path comprising:
(a) a reservoir of a medical fluid;
(b) a drip chamber in fluid communication with the reservoir; and,
II. a by-pass that circumvents the primary path and comprises means for releasably connecting thereto said by-pass comprising:
(c) an electrotransport apparatus for admitting a beneficial agent into the medical fluid, the electrotransport apparatus comprising:
(1) a housing comprising a wall that surrounds an internal space;
(2) an inlet in the wall adapted for receiving fluid from the primary path;
(3) an outlet in the wall adapted for returning fluid to the primary path;
(4) a pair of electrodes in spaced-apart position within the lumen;
(5) an ion exchange membrane interposed between the electrodes; and,
(6) a beneficial agent in the lumen between the wall and the ion exchange membrane.

27. The parenteral delivery system for administering the beneficial agent according to claim 26, wherein the electrodes are connected to an electrical power source.

28. The parenteral delivery system for administering the beneficial agent according to claim 26, wherein a fluid passageway is in the lumen extending from the inlet to the outlet.

29. The parenteral delivery system for administering the beneficial agent according to claim 28, wherein one of the electrodes is in the passageway.

30. The parenteral delivery system for administering the beneficial agent according to claim 28, wherein an additional ion exchange membrane is present in the lumen, and passageway is between the ion exchange membranes.

* * * * *